United States Patent [19]
Chow et al.

[11] Patent Number: 5,891,448
[45] Date of Patent: Apr. 6, 1999

[54] CONTROL OF CALCIUM FLUORIDE FORMATION IN MOUTH RINSES, DENTIFRICES AND GELS

[75] Inventors: Laurence C. Chow, Potomac; Shozo Takagi, Gaithersburg, both of Md.

[73] Assignee: American Dental Association Health Foundation, Caithersburg, Md.

[21] Appl. No.: 741,333

[22] Filed: Oct. 29, 1996

Related U.S. Application Data

[63] Continuation of Ser. No. 369,744, Jan. 6, 1995, abandoned.

[51] Int. Cl.$^6$ ..................................................... A61K 9/00
[52] U.S. Cl. .......................... 424/400; 424/468; 424/464; 424/48; 424/49; 424/52
[58] Field of Search ..................................... 424/400, 440, 424/445, 434, 435

[56] References Cited

U.S. PATENT DOCUMENTS

| | | |
|---|---|---|
| 3,966,863 | 6/1976 | Forward et al. ............................ 424/52 |
| 4,048,300 | 9/1977 | Tomlinson et al. . |
| 4,080,440 | 3/1978 | Dibiulio et al. . |
| 4,083,955 | 4/1978 | Grabenstetter et al. . |
| 4,108,980 | 8/1978 | Duff . |
| 4,177,258 | 12/1979 | Gaffar et al. . |
| 4,183,915 | 1/1980 | Gaffar et al. . |
| 4,283,385 | 8/1981 | Dhabhar et al. . |
| 4,348,381 | 9/1981 | Gaffar . |
| 4,397,837 | 8/1983 | Raaf et al. . |
| 4,420,312 | 12/1983 | Wason ....................................... 51/308 |
| 4,460,565 | 7/1984 | Weststrate et al. . |
| 4,532,124 | 7/1985 | Peasce . |
| 4,556,561 | 12/1985 | Brown et al. . |
| 4,606,912 | 8/1986 | Rudy et al. . |
| 4,610,873 | 9/1986 | Rudy et al. . |
| 4,714,608 | 12/1987 | Rolla . |
| 4,861,590 | 8/1989 | Grodberg . |
| 5,143,719 | 9/1992 | Elliott et al. .............................. 424/52 |
| 5,145,668 | 9/1992 | Chow et al. . |
| 5,310,542 | 5/1994 | Av et al. ................................... 424/52 |
| 5,476,647 | 12/1995 | Chow et al. .............................. 424/52 |

FOREIGN PATENT DOCUMENTS

| | | | |
|---|---|---|---|
| 089136 | 9/1983 | European Pat. Off. | ......... A61K 7/16 |
| 263638 | 4/1988 | European Pat. Off. | ......... A61K 7/16 |
| WO9010435 | 9/1990 | WIPO | .............................. A61K 7/18 |
| WO9507685 | 3/1995 | WIPO | .............................. A61K 7/16 |

OTHER PUBLICATIONS

Chow, L.C. and Takagi, S. (1991): Deposition of Fluoride on Tooth Surfaces by A Two–solution Mouth Rinse In Vitro. Caries Res, 25:397–401.

Chow, L.C., Takagi, S., and Shih, S. (1992): Effect of A Two–solution Fluoride Mouth Rinse on Remineralization of Enamel Lesions In Vitro, J. Dent Res, 77:443–447.

Vogel, G.L., Mao, Y., Carey, C.M., Chow, L.C. and Takagi, S. (1992): In Vivo Fluoride Concentrations Measured for Two Hours After a NaF or a New Two–Solution Rinse, J. Dent Res, 71:448–452.

(List continued on next page.)

*Primary Examiner*—Thurman K. Page
*Assistant Examiner*—William E. Benston, Jr.
*Attorney, Agent, or Firm*—Banner & Witcoff, Ltd.

[57] ABSTRACT

Specific compositions and methods are disclosed employing calcium fluoride inhibitors in two-component fluoride delivery systems to produce an initial delay in calcium fluoride formation and to control the rate of reactions that precipitate calcium fluoride in order to achieve enhanced fluoride deposition in the oral environment. In the two-component fluoride delivery system, one component contains a source of calcium ions and the other a source of fluoride ions. An inhibitor of calcium fluoride formation is present in one or both phases such that when one or both components are mixed the formation of calcium fluoride precipitate does not occur until at least about five seconds after mixing. The system may be employed in the form of mouth rinses, dentifrices, or chewable tablets.

26 Claims, 2 Drawing Sheets

OTHER PUBLICATIONS

Amjad, Z. (1993): Performance of Inhibitors in Calcium Fluoride Crystal Growth Inhibition, Langmuir, 9:597–600.

Grases, F., et al. (1991): A Study of the Relationship Between the Chemical Structure of Some Carboxylic Acids and Their Capacity to Inhibit the Crystal Growth of Calcium Fluoride. Colloids Surf., 54:313–319.

Grases, F., et al., (1991): Determination of Citric Acid Based on Inhibition of the Crystal Growth of Calcium Fluoride, Analyst, 116:59–63.

Amjad, Z. (1991): Constant Composition Study of Crystal Growth of Calcium Fluoride. Influence of Polycarboxylic Acids, Polyphosphates, Phosphonates, and Phytate, Langmuir, 7:600–603.

Christofferson, J., et al. (1988): Kinetics of Dissolution and Growth of Calcium Fluoride and Effects of Phosphate, Acta Odontol. Scand., 46:325–336.

Nancholas, G.H., et al. (1982): The Kinetics of Crystal Growth of Divalent Metal Fluorides, AIChE, Symp. Ser. 78:26–36.

Rolla, G. and Sazegaard, E. (1990): Critical Evaluation of The Composition and Use of Topical Fluorides, With Emphasis On The Role of Calcium Fluoride In Caries Inhibition, J Dent Res 69 (Spec Iss): 780–785.

Sieck, B; Takagi, S.; and Chow, L.C. (1990): Assessment of Loosely–bound and Firmly–bound Fluoride Uptake by Tooth Enamel From Topically Applied Fluoride Treatments, J Dent Res, 60:1261–1265.

CONTROL OF CALCIUM FLUORIDE FORMATION IN MOUTH RINSES, DENTIFRICES AND GELS

This application is a continuation of application Ser. No. 08/369,744, filed Jan. 6, 1995, now abandoned.

BACKGROUND OF THE INVENTION

This invention was supported in part by research Grant No. DE05354 to the American Dental Association Health Foundation from the National Institute of Dental Research. The Government has certain rights in this invention.

FIELD OF THE INVENTION AND DESCRIPTION OF THE PRIOR ART

Self-applied fluorides (F) in the forms of rinses and dentifrices are widely used in this country and elsewhere in the world. They have been shown to be effective in reducing tooth decay. The F containing mouth rinses formulated for daily use usually contain 250 parts per million (ppm) of F as sodium fluoride or stannous fluoride. The F dentifrices typically contain 1000 ppm of F as sodium fluoride or sodium monofluorophosphate. The cariostatic effects of both of these F regimens are believed to derive from their ability to deposit F on the surfaces of teeth and other tissues in the mouth. Although the deposited F is labile in nature and is easily leached out, the daily application of either the rinse or dentifrice can produce and maintain an elevated level of F in the mouth.

It was previously demonstrated (Chow, L. C. and Takagi, S. (1991): Deposition of Fluoride on Tooth Surfaces by a Two-solution Mouth Rinse In Vitro. Caries Res, 25:397–401) that a 1-minute rinse application with a sodium fluoride rinse that contained 250 ppm of F deposited 0.34 $\mu g/cm^2$ of F, and a 1-minute brushing with a NaF dentifrice that contained 1000 ppm of F deposited 0.25 $\mu g/cm^2$ of F on the tooth surface. Based on the recommended quantity for the rinse (10 ml) or for the dentifrice (1 gram) per application and the total surface area of the teeth in the mouth, it was estimated that less than 0.5% of the F in the rinse or the dentifrice is deposited on the teeth. Thus, nearly all of the fluoride remains in the rinse or dentifrice that is expectorated. Although numerous fluoride formulations have been described in the scientific and patent literature, with a few exceptions, none has incorporated into its formulation reaction mechanisms that cause substantial amounts of the fluoride to precipitate out of the delivery medium and deposit on or into dental tissues.

Chow and Takagi (U.S. Pat. No. 5,145,668) developed a novel system consisting of two components (solutions or pastes). When the two components are brought in contact, a rapid but controlled reaction precipitates calcium fluoride continuously within about a 1-minute time period. Component A contains a soluble calcium salt (e.g., $CaCl_2$) and a pH buffer (e.g., sodium acetate), and component B contains a complex F compound (e.g., $Na_2 SiF_6$). Each component is stable for indefinite periods in the absence of the other. When the two components are combined, hydrolysis of the complex F will occur which produces sufficient amounts of free F to cause calcium fluoride precipitation. This in turn keeps the free F concentration in the mixture sufficiently low to allow continued hydrolysis of the complex F compound and precipitation of calcium fluoride. The $H^+$ ions, a byproduct of the complex F hydrolysis, are consumed by the pH buffer so that the pH of the rinse remains near neutral. With proper concentrations of calcium and complex F in the two solutions, a significant amount of calcium fluoride can be deposited on the tooth surface within the approximately 1-minute application time. The chemical reactions that occur in the two-component system may be described by the following equations:

$$SiF_6^{2-} + 2H_2O \rightarrow SiO_2 + 6F + 4H^+ \quad (1)$$

$$3Ca^{2+} + 6F \rightarrow 3CaF_2 \quad (2)$$

The superior efficacies of this two-component system have been demonstrated in studies published in the scientific literature. Chow, L. C. and Takagi, S. (1991): Deposition of Fluoride on Tooth Surfaces by A Two-solution Mouth Rinse In Vitro. Caries Res, 25:397–401; Chow, L. C., Takagi, S., and Shih, S. (1992): Effect of A Two-solution Fluoride Mouth Rinse on Remineralization of Enamel Lesions In Vitro, J. Dent Res, 77:443–447; Vogel, G. L., Mao, Y., Carey, C. M., Chow, L. C. and Takagi, S. (1992): In Vivo Fluoride Concentrations Measured for Two Hours After a NaF or a New Two-Solution Rinse, J. Dent Res, 71:448–452.

One significant disadvantage of the two-component F system described above is that it requires the use of a complex F that has a specific hydrolytic property. The compounds known to be suitable for this purpose include the salts of fluorosilic acid ($H_2SiF_6$) and fluorostannic acid ($H_2SnF_6$). Because none of the suitable complex F salts are currently approved by the Federal Food and Drug Administration for use in rinses, dentifrices, and other oral health care products, a great deal of work would be required to demonstrate safety, in addition to efficacy, before these F compounds may be used clinically.

Chow and Takagi discovered (U.S. patent application Ser. No. 08/120,586) another novel two-component system that is capable of producing increased F deposition and is comprised of FDA approved fluoride compounds. Component A of the system contains a soluble calcium source and a soluble Ca-complexing anion such as ethylene diaminetetraacetic acid (EDTA). The calcium in this phase is largely bound to the Ca-complexing agent. Component B contains an FDA approved F compound such as sodium fluoride or stannous fluoride. When the two components are combined, precipitation of calcium fluoride ($CaF_2$) removes free $Ca^{2+}$ from the solution. This causes the release of additional free $Ca^{2+}$ from the calcium binding agent which, in turn, allows additional $CaF_2$ to precipitate. Thus, the chemical reactions that occur in this two-component system may be represented by the following equations:

$$Ca^{2+} + 2F \rightarrow CaF_2 \quad (3)$$

$$CaH(EDTA)^+ \rightarrow Ca^{2+} + H(EDTA)^{2-} \quad (4)$$

Although all of the components in the above system are on the FDA's lists of approved food additives and/or approved ingredients for oral health care products, the use of a strong Ca-complexing agent, EDTA, in a product designed for daily applications is of some concern.

There are many other disclosures in the literature of dental treatments involving the use, at least optionally, of fluoride, often in the context of tooth remineralization. For example, U.S. Pat. No. 4,556,561 discloses solutions, gels, and substantially nonaqueous dispersions that form dicalcium phosphate dihydrate under appropriate conditions, as well as methods of their use. These compositions are useful in topically fluoridating and/or mineralizing dental tissue, such as enamel, dentin, and exposed root surfaces. The incorporated fluoride is in the form of $Ca_5(PO_4)_3F$ and is more permanently retained than $CaF_2$ and other fluoridation products.

U.S. Pat. No. 4,048,300 discloses a single dental preparation including a material containing calcium and phosphorous. The calcium/phosphorous containing component may also include fluoride. Examples of calcium/phosphorous/fluoride components include fluorapatite, fluorohydroxyapatite, apatite, calcium deficient apatite, and hydroxyapatite substituted by a fluoranion. This component is useful in a dental cream.

U.S. Pat. No. 4,080,440 discloses a method for the remineralization of tooth enamel using a two solution system. The first solution is a cationic solution containing a calcium salt and optionally a heavy metal cation. The second solution is an anionic solution containing a phosphate salt and optionally non-phosphatic anions including fluoride ions. The pH of the solutions ranges from 2 to 4 and the ratio of calcium to phosphorous ranges from 0.01 to 100. The solution, produced by mixing the two-components, is described as a "metastable" solution and requires a residence time in the mouth of from 10 seconds to about 3 minutes in order to raise the pH of the solution such that the components of the solution precipitate in the tooth resulting in enamel remineralization.

U.S. Pat. No. 4,803,955 describes a two-step process for remineralizing dental enamel. In the process, two solutions, one comprising a calcium salt, and the other solution comprising a phosphorous salt along with an optional fluoride salt, are sequentially contacted with dental enamel. The sequential solution contact results in the surface of the enamel being remineralized.

U.S. Pat. No. 4,108,980 describes a process for applying fluoride to teeth with a material having calcium and phosphate components. The dental material includes a salt which ionizes to produce fluoride ions. The formulations described in this invention are made well in advance of application to tooth surfaces.

U.S. Pats. Nos. 4,177,258 and 4,183,915 describe stable solutions for dental remineralization. The solutions include a source of calcium ions, a source of phosphate ions and a source of fluoride. The solutions also include an anti-nucleating agent consisting of diamine tetramethylenephosphonic acids having a specific formula. The anti-nucleating agent stabilizes the calcium ions and phosphorous ions and prevents them from precipitating as large, insoluble apatite crystals by absorbing onto spherical nucleated particles as they form and blocking crystal growth.

U.S. Pat. No. 4,348,381 describes remineralization solutions similar to those described in the '258 and '915 patents above. However, the anti-nucleating agent of the '381 solution is PBTA and its water soluble salts.

U.S. Pat. No. 4,397,837 describes a two-phase dental composition in which the two phases are combined when applied to teeth. The first phase of the composition includes a calcium component. The second phase includes a water soluble phosphate component and a water soluble fluoride component.

U.S. Pat. No. 4,460,565 describes a remineralizing dentifrice composition. The composition includes a calcium containing component, two fluoride components, an alkali or alkaline earth metal fluoride and an alkali metal fluorophosphate, two phosphate components, a soluble cyclic alkali metal phosphate and a soluble linear phosphate.

U.S. Pat. No. 4,532,124 describes a dental rinse. The dental rinse includes water soluble salts of fluorine, calcium and phosphorous. The composition additionally includes a substance metabolized into an alkali, such as urea, which raises the solution pH causing calcium precipitation.

U.S. Pats. Nos. 4,606,912 and 4,610,873 describe a clear, stable aqueous mouthwash free of calcium phosphate crystals. The mouthwash includes a chelating agent in combination with a calcium ion source, and a phosphate ion source. The calcium ion source consists of a component capable of providing fluoride ions. The aqueous composition contains calcium ions, phosphate ions, and fluoride ions.

U.S. Pat. No. 4,714,608 describes an aqueous dental preparation. The dental preparation includes a fluoride component in a solution having a pH less than 2. The compound can be applied to teeth either before or after the teeth are treated with calcium. This provides for the precipitation of $CaF_2$ as a thin homogeneous layer on the tooth enamel.

U.S. Pat. No. 4,861,590 describes a sustained release fluoride in calcium composition. The composition includes MFP (monofluorophosphate) and an ionizable calcium source. Sodium fluoride may be added to the composition as desired.

U.S. Pat. No. 4,283,385 describes dentifrices containing insoluble calcium compounds utilized as abrasive dentifrices with a minor amount of EDTA or its sodium salts. Also included in this single component dentifrice is a fluoride compound, preferably sodium monofluorophosphate.

In addition, a number of calcium fluoride crystal growth inhibitors have been reported in the literature. Amjad, Z. (1993): Performance of Inhibitors in Calcium Fluoride Crystal Growth Inhibition, Langmuir, 9:597–600; Grases, F., et al. (1991): A Study of the Relationship Between the Chemical Structure of Some Carboxylic Acids and Their Capacity to Inhibit the Crystal Growth of Calcium Fluoride. Colloids Surf., 54:313–319; Grases, F., et al., (1991): Determination of Citric Acid Based on Inhibition of the Crystal Growth of Calcium Fluoride, Analyst, 116:59–63; Amjad, Z. (1991): Constant Composition Study of Crystal Growth of Calcium Fluoride. Influence of Polycarboxylic Acids, Polyphosphates, Phosphonates, and Phytate, Langmuir, 7:600–603; Christofferson, J., et al. (1988): Kinetics of Dissolution and Growth of Calcium Fluoride and Effects of Phosphate, Acta Odontol. Scand., 46:325–336; Nancholas, G. H., et al. (1982): The Kinetics of Crystal Growth of Divalent Metal Fluorides, AIChE Symp. Ser. 78:26–36.

Consequently, there exists a need to develop a two-component fluoride delivery system that is effective as well as totally acceptable from the safety viewpoint.

SUMMARY OF THE INVENTION

In summary, the invention provides specific methods to use calcium fluoride inhibitors in two-component fluoride delivery systems to produce an initial delay in calcium fluoride formation and to control the rate of reactions that precipitate calcium fluoride with the objective of achieving enhanced fluoride deposition in the oral environment.

More particularly, this invention comprises a two-phase fluoride delivery system in which one phase contains a source of calcium ions and the other a source of fluoride ions. An inhibitor of calcium fluoride formation is also present in one or both phases. When the two phases are mixed, the formation of calcium fluoride precipitate will occur, but not until at least about 5 seconds after mixing. Preferably, the calcium fluoride precipitation reaction should continue such that by the end of the intended application time, at least about 25% of the dissolved fluoride in the delivery system is precipitated out. This system, when used in the form of mouth rinses, dentifrices, or chewable tablets, can deposit significantly more fluoride in the mouth than presently used formulations containing comparable amounts of fluoride. Thus, the new formulations based on this two-component system should be significantly more efficacious than those currently in use.

In its preferred form, the invention comprises a two-component system for delayed sustained precipitation of fluoride onto and into dental tissue, comprising (a) a first component containing a soluble calcium source, with no more than about ten percent of the calcium in complex form, and providing a calcium ion concentration of at least about 10 mmols per liter in the supersaturated solution ultimately formed by mixing the two components in an aqueous environment; (b) a second component, preferably separate, containing a soluble fluoride compound providing a fluoride concentration of at least about 3 mmol/L in the supersaturated solution ultimately formed by mixing the two components in an aqueous environment; and (c) a calcium fluoride inhibitor present in either or both of the two components (a) and (b). The calcium fluoride inhibitor is preferably an inhibitor of nucleation as well as crystal growth. When the two components are combined, the inhibitor produces a delay of at least about 5 seconds before significant formation of calcium fluoride precipitate occurs. Furthermore, the phosphate level in the system is less than the concentration needed for significant precipitation of hydroxyapatite (remineralization).

The invention also contemplates a method for fluoridating dental tissue comprising mixing the components of claim 1 and promptly (preferably immediately) applying the mixture to dental tissue.

It is an advantage of the present invention that it provides an initial delay in calcium fluoride formation so that the treatment mixture can enter into intimate contact with the dental surfaces undergoing fluoridation before precipitation of calcium fluoride begins to any significant extent.

It is also an advantage of the present invention that the use of inhibitors of calcium fluoride formation permits control of the rate of the reaction so that precipitation of calcium fluoride continues throughout the entire treatment period resulting in enhanced fluoride deposition.

In this regard, it is an advantage of the present invention that when used in the form of mouth rinses, dentifrices, or chewable tablets, it can deposit significantly more fluoride in the mouth than presently used formulations containing comparable amounts of fluoride.

It is a further advantage of the instant invention that compositions for the invention may be chosen which are wholly selected from materials that are approved by the FDA for oral use.

DESCRIPTION OF THE PREFERRED EMBODIMENTS

Figure 1:
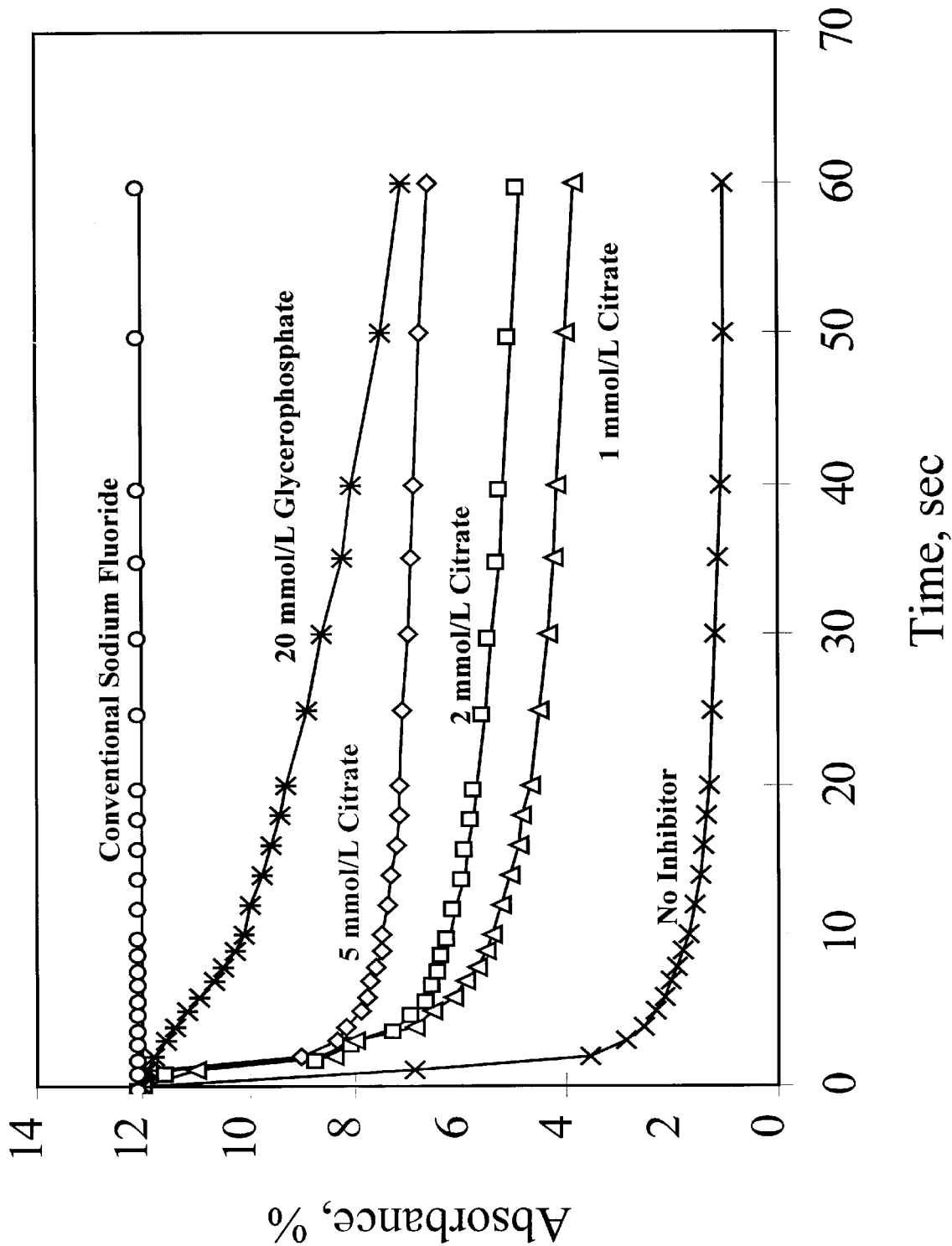
FIG. 1 shows fluoride concentration as a function of time for a variety of fluoridation formulations.

Calcium fluoride and "calcium fluoride like" deposits are the major reaction products between conventional topical fluoride agents (sodium fluoride, acidulated phosphate fluoride, etc.) and the tooth surface. The application of such a fluoride agent causes a small amount of tooth mineral to dissolve to produce the calcium needed for the formation of calcium fluoride. The two-component systems described above are in contrast to the conventional fluoride agents in that a fluoride source and a calcium source can be present separately in the two components initially. After the two components are combined, calcium fluoride forms by reaction between the fluoride and calcium, and these reactions occur whether or not tooth is present. An advantage of this system is that a much larger amount of fluoride (approximately 20 times) can be deposited on the tooth surface, probably because of the greater availability of calcium. The same reason may explain another advantage of the two-component system: a large amount of calcium fluoride is also deposited in plaque by the two-component system and not by conventional fluoride agents of the same fluoride content.

In order to accomplish a large fluoride deposition, a two-component fluoride delivery system must produce a delay in the formation of calcium fluoride after the calcium- and fluoride-containing components are combined. This is because any calcium fluoride that is formed in the combined solution before the solution is in contact with the tooth or plaque would fail to be deposited. In the two previously disclosed two-component systems, this delay was produced by the use of a fluoride- or calcium-complexing system which made available only a small portion of the total amount of fluoride or calcium for the reaction at any given time, and the bound calcium or fluoride was released gradually as needed by the reaction.

In conventional fluoride systems, any agent, such as phosphate (in the form of $HPO_4^{2-}$), that interferes with the formation of calcium fluoride is considered undesirable because it would reduce the fluoride deposition. Rolla, G. and Sazegaard, E. (1990): Critical Evaluation of The Composition and Use of Topical Fluorides, With Emphasis On The Role of Calcium Fluoride In Caries Inhibition, J Dent Res 69 (Spec Iss): 780–785. It was discovered in the present invention that, in contrast to the conventional concept, calcium fluoride inhibitors, when present in either or both of the components in the two-component system, can, under controlled conditions, produce the desired delay in the formation of calcium fluoride. In addition to producing the initial delay, the inhibitors can also be used to control the rate of the calcium fluoride formation such that the reaction can continue throughout the application time. In the absence of an inhibitor, the reaction that forms calcium fluoride usually ends within 15 seconds. Experimental results show that to produce the desired fluoride deposition, there should be a minimum of 5 seconds of delay of calcium fluoride formation after the two components are combined. Preferably, at least 25% of the soluble fluoride initially present in the system should be precipitated out by the end of the intended application time (typically about 1 min.).

In accordance with the present invention, the first component of the two component system for delayed sustained precipitation of calcium fluoride contains a soluble calcium source providing a calcium ion concentration of at least about 10 mmols/L in the super-saturated solution formed by mixing the two components. The soluble calcium source will in general be a salt of calcium which is non-toxic enough for oral use at the intended level on a regular basis, and stable for the desired shelf life. Examples of appropriate calcium salts include calcium chloride, calcium acetate, calcium butylate, calcium lactate, and all other non-toxic salts of calcium and inorganic or organic acids which dissolve in aqueous solution to the extent stated above. Calcium acetate is employed near neutral pH so it does not introduce a buffering effect. A preferred calcium salt, exemplified herein, is calcium chloride.

The invention also contemplates a second component, isolated from reaction with the first during storage, containing a soluble fluoride compound providing a fluoride concentration of at least about 3 mmols per liter in the supersaturated solution formed by mixing the two components. Useful fluoride sources include compounds of the desired solubility which are non-toxic enough for oral use at the intended level on a regular basis, and stable for the desired shelf life. Examples of suitable fluorides include sodium fluoride, stannous fluoride and potassium fluoride. Preferred are the fluoride compounds already approved by the FDA for use in human oral health care, including NaF or $SnF_2$.

There are a large number of compounds that have been identified as calcium fluoride growth inhibitors and may be useful in the practice of the present invention. Examples include polyphosphates such as hexametaphosphate; phosphate; the polyphosphonate methylenephosphonic acid; the phosponocarboxylic acid 2-phospono-1, 2,4-butanetricarboxylic acid; pyrophosphates; the di-carboxylic acids fumaric, maleic, malic, malonic, oxalic, succinic, and tartaric; the tri-carboxylic acids tri-carballylic, benzene-1,3, 5-tricarboxylic (trimesic); the polyboxylic acid benzene-hexacarboxylic (mellitic); and glucose. The prior art studies investigating the inhibition of crystal growth of calcium fluoride mentioned in the Background of the Invention focused on the use of relatively low levels of compounds which delayed the crystal growth of calcium fluoride. It is believed that in the two-component fluoride system of the present invention, the delay in calcium fluoride formation is the result of inhibition of nucleation as well as crystal growth of calcium fluoride. Although in some cases crystal growth inhibitors are also effective nucleation inhibitors, in other cases they are not. The phosponate hydroxyethylidine-1,1-diphosponic acid (HEDP) and the polycarboxylic acid poly-acrylic acid have not exhibited utility in test results to date, but merit further study. We have identified some of the effective nucleation inhibitors and determined the conditions under which the inhibitors work efficaciously for purposes of the invention. Some specific examples include orthophosphates, pyrophosphates, phytate (a polyphosphate in which there are 12 phosphates), di-carboxylic acids (e.g., glycerophosphate), tri-carboxylic acids (e.g., citric acid), and tetra-carboxylic acids (e.g., EDTA).

In order to achieve the purposes of producing desired rates of calcium fluoride precipitation, the inhibitors disclosed in the present invention must be used under conditions that differ significantly from the conditions used in the studies cited above. Specifically:

(1) The concentrations of the inhibitors needed for the invention are generally considerably higher.

(2) Since the inhibition produced by a given agent often changes drastically with the pH and/or the inhibitor concentration, for many inhibitors the preferred pH and concentration need to be determined according to the criteria and examples set forth herein.

The previously published studies on calcium fluoride inhibition, e.g., employed citrate at a concentration of 0.00025 to 0.01 mmol/L to produce inhibition effects in calcium fluoride solutions with Ca and F concentrations of 0.5 mmol/L. In the inventive F delivery systems, the F concentration is about 3 mmols per liter or higher, and the Ca concentration is about 10 mmol/L or higher. Under these highly supersaturated conditions, a citrate concentration of 1 to 5 mmol/L (Table 6) is needed to produce a delay in calcium fluoride precipitation. In general, the concentrations of inhibitors needed in the instant system are 100 to 1000 times higher than those used in the previous studies.

The optimum concentration of each inhibitor varies with the pH and fluoride conditions of the treatment formulation. With a limited amount of routine testing along the lines described herein, one of ordinary skill in the art may adjust these parameters to produce the desired 5 second delay in significant calcium fluoride precipitation and to control the rate of the subsequent precipitation of calcium fluoride in the two component fluoride systems of the invention.

The general approach may be described as follows: The F and Ca concentrations are first selected before testing candidates for inhibitors. The F concentration in a particular regimen, e.g., mouth rinse for daily use, is determined based on considerations of efficacy, safety, and the like. Once a F concentration is selected, e.g., 228 ppm, solution B of the two-component system is prepared to have twice the desired F concentration, e.g., 456 ppm or 24 mmol/L. Test solutions for component A of the two-component rinse will then be prepared to contain a range of Ca concentrations. The optimum Ca concentration is selected based on the criteria (1) there is sufficient Ca to precipitate out most of the F, i.e., Ca concentration is one half that of F concentration for $CaF_2$ stoichiometry, (2) the degree of saturation with respect to $CaF_2$ should not be too low so that $CaF_2$ precipitation does not occur within the intended application time even in the absence of an inhibitor, and (3) degree of saturation with respect to $CaF_2$ should not be too high such that inhibitors would have too little effect on delay and the rate of $CaF_2$ precipitation. A tentative "optimum" Ca concentration, e.g., 20 mmol/L, is then selected. For a given combination of F and Ca, the following tests are conducted to determine the optimum conditions for each candidate of inhibitor.

Two important variables must be included in the tests for a given candidate of inhibitor:

1. The pH of the Ca- and F-containing solutions. Generally, the pH's of the two solutions are the same. Most of the inhibitors are multibase acids (acids that have more than one dissociable proton). Usually tests will be done at pH values approximately 1 unit below and above each pK such that the dominant acid anion species is well defined. The data presented in Tables 3, 4 and 9 illustrate the importance of controlling the pH in order to obtain a strong inhibition effect.

1 The concentration of the inhibitor. A large number of inhibitors exhibit strong inhibition effects only when the inhibitor's concentration falls within a narrow range. Some examples of this phenomenon are given in Tables 2 and 5. Thus, it is necessary to test the inhibition effects of a candidate compound over a reasonable range of concentrations, varying the concentration in small steps to ensure that the effective concentration is not overlooked.

It is important to note that, generally, for a given candidate compound, a particular dissociated species of the acid provides the strong inhibition effect when the concentration (activity) of that species falls within a narrow range. Since the concentration of such a species depends on both the concentration of the compound and the pH, it is highly likely that more than one combination of the pH and the inhibitor concentration will provide the optimum inhibition effect. This, in fact, is an advantage, because it will not limit the pH of the F regimen to a specific value.

Figure 2:
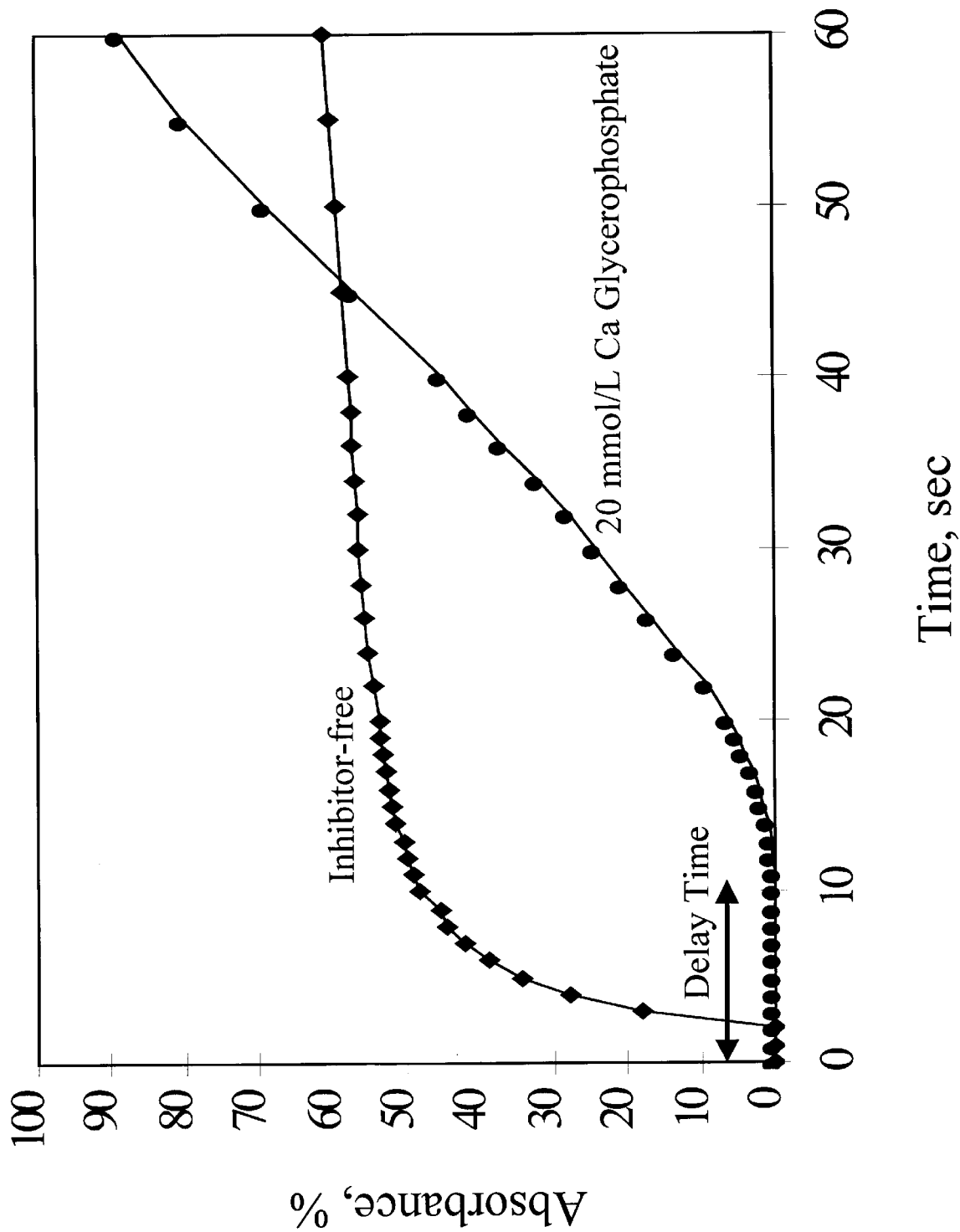
FIG. 2 illustrates the comparative delay in $CaF_2$ precipitation achieved with a specific embodiment of the present invention.

Two types of measurements are conducted to determine the potential effectiveness of a candidate inhibitor compound. The first test is to measure the delay in $CaF_2$ precipitation by a spectrophotometry method described below. FIG. 2 shows that $CaF_2$ precipitation occurred nearly instantaneously in a two-component rinse without an inhibitor. The same rinse with 20 mmol/L glycerophosphate as an inhibitor exhibited a delay of approximately 12 seconds. The next test is to measure the precipitation of $CaF_2$ by measuring the decrease in F concentration in the combined solution as described below. FIG. 1 shows that the F concentration decreased rapidly in the rinse without an inhibitor and the decrease was gradual when an effective inhibitor is present.

More specifically, for most inhibitors of $CaF_2$, there is a particular range of pH within which the inhibition effects are significantly stronger than outside that pH range. For example, pyrophosphate (0.05 mmol/L) produced an induction time of 16.7 seconds at pH 5.6 (Table 3) and a non-significant 1 second induction time (compared with the 1 to 2-second induction time when no inhibitors were present, Table 1) at pH 9.2. Phosphate (0.1 mmol/L) produced a small induction time (2.7 second) at pH 7 but a significant induction time of 11.7 seconds at pH 8.3. The dominant pyrophosphate species at pH 5.6 is $H_2P_2O_7^{2-}$, and the dominant phosphate species at pH 8.3 is $HPO_4^{2-}$. Thus, the data on induction time suggest that it is the anion with a 2− charges that produces the effective inhibition.

However, there are other inhibitors such as citrate and glycerophosphate that exhibit effective inhibition over a wider pH range. Although the species with 2− charge produce effective inhibition, inhibition was also observed when the dominant species has a charge of 1− or 3−. Some of the species, for example citrate, are not strong Ca-complexing agents, but their complexing abilities become stronger as the pH increases. Thus, some of the inhibitive effect observed at high pH's (when the dominant species has a charge of 3−) may partially be attributable to the decreased free Ca available for the $CaF_2$ formation. It is important to note that since citrate is not a strong Ca-complexing agent, there are always some citrate ions that are not bound to Ca at any pH. It appears to be essential to have some "free" (non-Ca-bound) citrate ions in order to produce the inhibition. This hypothesis is supported by the observations in the EDTA experiments described below.

EDTA (5 mmol/L) produced strong inhibition effects at pH 5.5 and 6.4 (dominant species $H_2EDTA^{2-}$) (Table 9), but no inhibition at pH 11 (dominant species $EDTA^{4-}$). EDTA has a very strong Ca-complexing effect. Since there is excess Ca (20 mmol/L) relative to EDTA (5 mmol/L), it is expected that at pH 11 nearly all of the EDTA is bound to Ca. Thus, despite that approximately half of the Ca in the rinse is bound to EDTA, no induction time was observed because there was no significant free EDTA to produce the inhibition. When EDTA concentration was increased to 10 mmol/L, strong to total inhibition of $CaF_2$ formation was observed at pH 6 to 11 because of the near total complexation of Ca by EDTA. This observation indicates that Ca complexation can play an important role provided there is appropriate complexation which is obtained by having the appropriate pH and a sufficient or excess EDTA (relative to Ca) present.

Although some of the $CaF_2$ inhibitors, e.g., EDTA, citrate, etc., used in the present system are also Ca-complexing agents, many other inhibitors, e.g., pyrophosphate, phosphate, phosphonates, etc., do not complex Ca (negligible Ca binding under the conditions used). When used as an inhibitor in the present system, the concentration of the former (EDTA, citrate, etc.), required is much lower than in the previous system of Ser. No. 08/120,586 and only a very small portion (about 10% or less) of the Ca is complexed. In general, in the complex-Ca system, unlike the present invention, a buffer was contained in the F solution to lower the pH and thus cause a release of bound Ca when the two components were combined. This is unnecessary in the present system.

As compared with the numerous prior art fluoridation and remineralization systems that contain Ca, P, and F, we have found that the phosphate concentration needed to act as an inhibitor in the invention is quite low, i.e., 0.1 mmol/L (Table 4), and it should never reach the 1 mmol/L level. In contrast, in the remineralization systems, the levels of Ca and P should be comparable to each other (to precipitate hydroxyapatite $(Ca_5(PO_4)_3OH)$). The concentrations of these ions are generally at 1 to 3 mol/L. In the system of the present invention, only a small amount of phosphate is present as an inhibitor, and the ratio of Ca to P is about 200.

The invention also contemplates a method for fluoridating dental tissue comprising mixing the two components discussed above and promptly applying the mixture to dental tissue. The two components may be applied in the form of a multi-component mouthwash or dentifrice, or in a chewable tablet. In a chewable tablet, the components need not be separated during storage, because it is only when the calcium and fluoride sources are in an aqueous environment that precipitation will occur. In the mouthwash and dentifrice, the two components should be separately stored, but may be simultaneously dispensed from a container designed to accomplish this. Such two-component dispensing containers are known in the art. The source of water for the aqueous environment in which the first and second components are mixed may be saliva, particularly for the chewable tablet, or may be supplied by the mouthwash or dentifrice itself, at least in part.

When the two components of the inventive system are combined, the inhibitor produces a delay of at least about five seconds before significant precipitation of calcium fluoride takes place. The delay in precipitation, or induction period, may be significantly longer as shown in the Tables. Interestingly, the decrease in fluoride concentration occurs more rapidly upon mixing the two components than does the precipitation of calcium fluoride as measured by a spectrophotometric test for turbidity. It is theorized that this may occur because small nuclei of calcium fluoride are forming in solution or soluble calcium-fluoride complexes are forming. During the induction period, the calcium and fluoride ions are believed to diffuse on and into the dental tissues. Precipitation of calcium fluoride which thereafter takes place is in intimate contact, therefore, with the intended site of deposition. The inhibitors also act to regulate the rate of precipitation of calcium fluoride so that it continues fairly steadily over the intended application time, generally on the order of 0.5 to 4 minutes, preferably about one minute. The following discussion of experimental results illustrates some of these points.

The induction times (delay in precipitation) of the two-component formulations containing various inhibitors were measured by a spectrophotometric method. Two milliliters each of component A (F-containing) and component B (Ca-containing) were combined and placed in a cuvette in the spectrophotometer. The absorbance at wavelength of 500 nanometers was measured. The time elapsed until the absorbance reached 0.01 was considered the induction time.

The induction times (in seconds, mean±s.d. of three measurements) for calcium fluoride precipitation produced by inhibitors under various conditions are shown in Tables 1–10.

Table 1 shows that in the absence of inhibitors, the induction time for calcium fluoride precipitation is short, i.e., 1 to 2 seconds.

TABLE 1

SHORT INDUCTION TIME IN SYSTEMS WITHOUT INHIBITOR:
INDUCTION TIMES AT TWO pH'S

| Component A | Component B | Induction Time (sec.) |
|---|---|---|
| 24 mmol/L NaF<br>pH 6 | 20 mmol/L CaCl$_2$<br>pH 6 | 2 ± 0 |
| 24 mmol/L NaF<br>pH 3 | 20 mmol/L CaCl$_2$<br>pH 3 | 1.7 ± 0.6 |

Under certain combinations of Ca and F concentrations, an induction time in CaF$_2$ precipitation may be obtained without the use of an added inhibitor. (The concept of utilizing inhibition of CaF$_2$ formation to produce enhanced F deposition also applies to such cases of self-inhibition.) As one may expect, for a given F concentration of the rinse, the conditions under which such "self-inhibition" occurs is very limited, and the use of one or more added inhibitors to obtain the desired induction time would be preferred for most F concentrations. The following is an example of an induction time with no added inhibitor:

Solution A: 40 mmol/L in CaCl$_2$, 100 mmol/L in KCl, pH 7

Solution B: 12 mmol/L in NaF, 100 mmol/L in KCl, pH 7

An induction time of 6±1 seconds (n=3) was obtained from the above solutions which did not contain an added inhibitor. The F deposition from this rinse was 0.67±0.30 μg/cm$^2$. This example also shows that by having a suitable induction time, the F deposition produced by this rinse is nearly three times that produced by a rinse that has twice as much F (See Example I).

Table 2 shows that pyrophosphate is an effective inhibitor for calcium fluoride precipitation. There is an optimum pyrophosphate concentration, at these conditions, between 0.025 to 0.1 mmol/L. The inhibition effect is small if the concentration is below or above the optimum range. An induction time of over 16 seconds can be obtained from pyrophosphate inhibitor.

TABLE 2

OPTIMUM CONCENTRATION FOR PYROPHOSPHATE
AT pH 5.6 IS BETWEEN 0.025 TO 9.1 mmol/L

| Component A | Component B | Induction Time (sec.) |
|---|---|---|
| 24 mmol/L NaF<br>pH 5.6<br>0.01 mmol/L pyrophosphate | 20 mmol/L CaCl$_2$<br>pH 5.6 | 3.0 ± 0 |
| 24 mmol/L NaF<br>pH 5.6<br>0.025 mmol/L pyrophosphate | 20 mmol/L CaCl$_2$<br>pH 5.6 | 5.3 ± 0.6 |
| 24 mmol/L NaF<br>pH 5.6<br>0.05 mmol/L pyrophosphate | 20 mmol/L CaCl$_2$<br>pH 5.6 | 16.7 ± 0.6 |
| 24 mmol/L NaF<br>pH 5.6<br>0.1 mmol/L pyrophosphate | 20 mmol/L CaCl$_2$<br>pH 5.6 | 14.0 ± 1.0 |
| 24 mmol/L NaF<br>pH 5.6<br>0.25 mmol/L pyrophosphate | 20 mmol/L CaCl$_2$<br>pH 5.6 | 3.5 ± 0.7 |
| 24 mmol/L NaF<br>pH 5.6<br>0.5 mmol/L pyrophosphate | 20 mmol/L CaCl$_2$<br>pH 5.6 | 3 ± 0 |
| 24 mmol/L NaF<br>pH 5.6<br>1 mmol/L pyrophosphate | 20 mmol/L CaCl$_2$<br>pH 5.6 | 2 ± 0 |
| 24 mmol/L NaF<br>pH 5.6<br>5 mmol/L pyrophosphate | 20 mmol/L CaCl$_2$<br>pH 5.6 | 1 ± 0 |

Table 3 shows that the inhibition effect of pyrophosphate is also sensitive to pH. Pyrophosphate has four pK's: 0.88, 2.0, 6.28, and 9.1. The data suggest that it is the H$_2$P$_2$O$_7^{2-}$ ions that has the inhibition effect. Thus, for pyrophosphate, the ideal pH range should be between pK$_2$ and pK$_3$, i.e., between 2.0 and 6.28.

TABLE 3

INHIBITION EFFECT OF PYROPHOSPHATE
DIMINISHES AT pH ABOVE 6

| Component A | Component B | Induction Time (sec.) |
|---|---|---|
| 24 mmol/L NaF<br>pH 5.6<br>0.05 mmol/L pyrophosphate | 20 mmol/L CaCl$_2$<br>pH 5.6 | 16.7 ± 0 |
| 24 mmol/L NaF<br>pH 9.2<br>0.05 mmol/L pyrophosphate | 20 mmol/L CaCl$_2$<br>pH 9.2 | 1.0 ± 0 |
| 24 mmol/L NaF<br>pH 5.6<br>0.1 mmol/L pyrophosphate | 20 mmol/L CaCl$_2$<br>pH 5.6 | 14.0 ± 1.0 |
| 24 mmol/L NaF<br>pH 6.4<br>0.1 mmol/L pyrophosphate | 20 mmol/L CaCl$_2$<br>pH 6.4 | 4.0 ± 0 |

Table 4 shows that the inhibition effect of phosphate is also sensitive to pH. The ideal pH seems to be above 6–7 and below 9. An induction time of approximately 12 seconds was obtained.

TABLE 4

INHIBITION EFFECT OF PHOSPHATE VARIES WITh pH

| Component A | Component B | Induction Time (sec.) |
|---|---|---|
| 24 mmol/L NaF<br>pH 7<br>0.1 mmol/L phosphate | 20 mmol/L CaCl$_2$<br>pH 7 | 2.7 ± 0.6 |
| 24 mmol/L NaF<br>pH 7.5<br>0.1 mmol/L phosphate | 20 mmol/L CaCl$_2$<br>pH 7.5 | 6.3 ± 1.2 |
| 24 mmol/L NaF<br>pH 8.3<br>0.1 mmol/L phosphate | 20 mmol/L CaCl$_2$<br>pH 8.3 | 11.7 ± 1.5 |
| 24 mmol/L NaF<br>pH 9.4<br>0.1 mmol/L phosphate | 20 mmol/L CaCl$_2$<br>pH 9.4 | 4 ± 2.8 |

Table 5 shows that there is an optimum concentration for glycerophosphate as an inhibitor. A maximum induction time of about 9 seconds was obtained with a glycerophosphate concentration of 20 mmol/L.

TABLE 5

OPTIMUM CONCENTRATION FOR GLYCEROPHOSPHATE IS BETWEEN 10 AND 40 mmol/L AT pH 6.2

| Component A | Component B | Induction Time (sec.) |
|---|---|---|
| 24 mmol/L NaF pH 6.2 | 20 mmol/L CaCl$_2$ pH 6.2 0.5 mmol/L glycerophosphate | 2.0 ± 0 |
| 24 mmol/L NaF pH 6.2 | 20 mmol/L CaCl$_2$ pH 6.2 1 mmol/L glycerophosphate | 3.3 ± 0.6 |
| 24 mmol/L NaF pH 6.2 | 20 mmol/L CaCl$_2$ pH 6.2 2 mmol/L glycerophosphate | 5.0 ± 0 |
| 24 mmol/L NaF pH 6.2 | 20 mmol/L CaCl$_2$ pH 6.2 5 mmol/L glycerophosphate | 5.7 ± 0.6 |
| 24 mmol/L NaF pH 6.2 | 20 mmol/L CaCl$_2$ pH 6.2 10 mmol/L glycerophosphate | 6.7 ± 0.6 |
| 24 mmol/L NaF pH 6.2 | 20 mmol/L CaCl$_2$ pH 6.2 20 mmol/L glycerophosphate | 8.7 ± 1.5 |
| 24 mmol/L NaF pH 6.2 | 20 mmol/L CaCl$_2$ pH 6.2 40 mmol/L pyrophosphate | 4.3 ± 0.6 |

Table 6 shows that with citrate as the inhibitor, the induction time increases continuously with increasing citrate concentration. An induction time of 16 seconds was obtained with 5 mmol/L of citrate, but calcium fluoride precipitation was totally inhibited at 10 mmol/L of citrate.

TABLE 6

INDUCTION TIME INCREASES WITH INCREASING CITRATE CONCENTRATION AT pH 6.2 CALCIUM FLUORIDE PRECIPITATION WAS TOTALLY INHIBITED AT 10 mmol/L CITRATE

| Component A | Component B | Induction Time (sec.) |
|---|---|---|
| 24 mmol/L NaF pH 6.2 | 20 mmol/L CaCl$_2$ pH 6.2 0.2 mmol/L citrate | 2.7 ± 0.6 |
| 24 mmol/L NaF pH 6.2 | 20 mmol/L CaCl$_2$ pH 6.2 0.5 mmol/L citrate | 6.0 ± 0 |
| 24 mmol/L NaF pH 6.2 | 20 mmol/L CaCl$_2$ pH 6.2 1 mmol/L citrate | 6.3 ± 0.6 |
| 24 mmol/L NaF pH 6.2 | 20 mmol/L CaCl$_2$ pH 6.2 2 mmol/L citrate | 8.7 ± 0.6 |
| 24 mmol/L NaF pH 6.2 | 20 mmol/L CaCl$_2$ pH 6.2 5 mmol/L citrate | 16.0 ± 0 |
| 24 mmol/L NaF pH 6.2 | 20 mmol/L CaCl$_2$ pH 6.2 10 mmol/L citrate | NO PPT. |

Table 7 shows that for a given citrate concentration of 2 mmol/L, the induction time increases with pH.

TABLE 7

INDUCTION TIME AT A GIVEN CITRATE CONCENTRATION INCREASES WITH INCREASING pH

| Component A | Component B | Induction Time (sec.) |
|---|---|---|
| 24 mmol/L NaF pH 2.4 | 20 mmol/L CaCl$_2$ pH 2.4 2 mmol/L citrate | 7.3 ± 0.6 |
| 24 mmol/L NaF pH 6.2 | 20 mmol/L CaCl$_2$ pH 6.2 2 mmol/L citrate | 8.7 ± 0.6 |
| 24 mmol/L NaF pH 7.3 | 20 mmol/L CaCl$_2$ pH 7.3 2 mmol/L citrate | 12.7 ± 1.2 |
| 24 mmol/L NaF pH 9.2 | 20 mmol/L CaCl$_2$ pH 9.2 2 mmol/L citrate | 15.0 ± 4.6 |

Table 8 shows that with EDTA as the inhibitor, the induction time also increases continuously with the EDTA concentration. An induction time of 19.5 seconds was obtained with 5 mmol/L of EDTA. However, calcium fluoride precipitation was completely inhibited at 10 mmol/L of EDTA.

TABLE 8

INDUCTION TIME INCREASES WITH INCREASING EDTA CONCENTRATION CALCIUM FLUORIDE PRECIPITATION WAS TOTALLY INHIBITED AT 10 mmol/L EDTA

| Component A | Component B | Induction Time (sec.) |
|---|---|---|
| 24 mmol/L NaF pH 5.5 | 20 mmol/L CaCl$_2$ pH 5.5 0.2 mmol/L EDTA | 2.0 ± 0 |
| 24 mmol/L NaF pH 5.5 | 20 mmol/L CaCl2 pH 5.5 0.5 mmol/L EDTA | 3.7 ± 0.6 |
| 24 mmol/L NaF pH 5.5 | 20 mmol/L CaCl$_2$ pH 5.5 1 mmol/L EDTA | 5.0 ± 0 |
| 24 mmol/L NaF pH 5.5 | 20 mmol/L CaCl$_2$ pH 5.5 2 mmol/L EDTA | 8.0 ± 0 |
| 24 mmol/L NaF pH 5.5 | 20 mmol/L CaCl$_2$ pH 5.5 5 mmol/L EDTA | 19.7 ± 1.5 |
| 24 mmol/L NaF pH 5.5 | 20 mmol/L CaCl$_2$ pH 5.5 10 mmol/L EDTA | NO PPT. |

Table 9 shows that the inhibition of EDTA is sensitive to pH. The induction time dropped sharply at pH 10 and above.

TABLE 9

INHIBITION EFFECTS OF EDTA DIMINISH ABOVE pH II

| Component A | Component B | Induction Time (sec.) |
|---|---|---|
| 24 mmol/L NaF pH 5.5 | 20 mmol/L CaCl$_2$ pH 5.5 5 mmol/L BDTA | 19.7 ± 1.5 |
| 24 mmol/L NaF pH 6.4 | 20 mmol/L CaCl$_2$ pH 6.4 5 mmol/L EDTA | 20 ± |
| 24 mmol/L NaF pH 10 | 20 mmol/L CaCl$_2$ pH 10 5 mmol/L BDTA | 9 ± |
| 24 mmol/L NaF pH 11 | 20 mmol/L CaCl$_2$ pH 11 5 mmol/L EDTA | 1 ± 0 |

Either the first component, the second component or both may contain at least one inhibitor. More than one inhibitor may be employed in some systems, and can result in a synergistic effect. Table 10 shows that certain inhibitors produce such a synergistic inhibition effect. An induction time of 44.5 seconds was obtained with the use of both pyrophosphate and EDTA for induction, whereas the induction time produced by the individual compounds are 16.7 and 8.0, respectively.

TABLE 10

SYNERGISTIC INHIBITION EFFECTS OF PYROPHOSPHATE AND EDTA

| Component A | Component B | Induction Time (sec.) |
|---|---|---|
| 24 mmol/L NaF pH 5.6 0.05 mmol/L pyrophosphate | 20 mmol/L CaCl$_2$ pH 5.6 | 16.7 ± 0.6 |
| 24 mmol/L NaF pH 5.5 | 20 mmol/L CaCl$_2$ pH 5.5 2 mmol/L EDTA | 8.0 ± 0 |
| 24 mmol/L NaF pH 5.6 0.05 mmol/L pyrophosphate | 20 mmol/L CaCl$_2$ pH 5.5 2 mmol/L EDTA | 44.5 ± 0.7 |

In separate experiments, the rates of subsequent calcium fluoride precipitation were measured with a specific F electrode. In this measurement, the F concentration of the combined solutions was recorded with time. For the 2-component formulations 10 mL each of components A(24 mmol/L NaF; 100 mmol/L KCl) and B(20 mmol/L CaCl$_2$; 100 mmol/L KCl) were combined. Citric acid was added to component B and the pH of the solutions was adjusted to 6.4. Glycerol phosphoric acid was added to component B and pH was adjusted to 7.0. In the ideal formulation the F concentration should decrease gradually and continuously such that all of the fluoride is precipitated at the end of the intended application time. The observed rates of calcium fluoride precipitation, expressed as decreases in the F concentrations, as affected by the inhibitors, are shown in FIG. 1. The F concentration decreases rapidly in the formulation where no inhibitor was present. In comparison, the decrease in F concentration was more gradual as the concentration of an inhibitor, citrate, increased from 1 to 5 mmol/L. In a conventional F formulation, e.g., NaF, the F concentration remained unchanged because of the lack of a mechanism to precipitate calcium fluoride. Again, the drop in F concentration leads the CaF$_2$ precipitation.

It is important to note that the data described above were obtained from systems that contain 24 mmol/L of NaF, a F concentration in the range of fluoride levels found in dentifrices and rinses presently available commercially. The inventive system of using calcium fluoride inhibitors to cause a delay in calcium fluoride precipitation is equally applicable to two-component systems that contain a higher or lower F concentration, although the preferred condition for each inhibitor will be different and can be determined for each fluoride concentration by the methods set forth herein.

The following examples show the F deposition produced by rinse formulations that incorporated a calcium fluoride inhibitor. The experimental rinses consisted of two aqueous solutions: solution A contained a source of calcium and solution B contained a source of fluoride. The two solutions were mixed and immediately applied to enamel surfaces for one minute as described previously. Chow, L. C. and Takagi, S. (1991): Deposition of Fluoride on Tooth Surfaces by a Two-solution Mouth Rinse In Vitro, Caries Res, 25:397–401. A constant composition fluoride titration method (Sieck, B; Takagi, S.; and Chow, L. C. (1990): Assessment of Loosely-bound and Firmly-bound Fluoride Uptake by Tooth Enamel From Topically Applied Fluoride Treatments, J Dent Res, 60:1261–1265) was used to measure the F deposition on tooth surfaces by the above 2-component rinse and a NaF rinse that contained 228 ppm of F.

EXAMPLE I

This example shows that when neither the calcium nor the fluoride was complexed and no CaF$_2$ inhibitor was present, the F deposition was low.

Solution A: 20 mmol/L in CaCl$_2$
Solution B: 24 mmol/L in NaF
The mean (n=3) F deposition was 0.24±0.09 $\mu$g/cm$^2$.

EXAMPLE II

Solution A: 20 mmol/L in CaCl$_2$, 2 mmol/L in citric acid, 100 mmol/L in KCl, pH adjusted to 5.7 with KOH.
Solution B: 24 mmol/L in NaF, 100 mmol/L in KCl, pH at 6.2.
Citric acid serves as a calcium fluoride inhibitor and also a calcium complexing agent.
The mean (n=3) F deposition was 2.65±0.36 $\mu$g/cm$^2$.

EXAMPLE III

Solution A: 20 mmol/L in CaCl$_2$, 100 mmol/L in KCl, pH adjusted to 7.9 with KOH.
Solution B: 24 mmol/L in NaF, 0.04 mmol/L in K$_2$HPO$_4$, 100 mmol/L in KCl, pH adjusted to 9.4 with KOH.
Phosphate acts as a calcium fluoride inhibitor. The mean (n=3) F deposition was 1.23±0.17 $\mu$g/cm$^2$.

EXAMPLE IV

Solution A: 20 mmol/L in CaC$_2$, 100 mmol/L in aspartic acid, 100 mmol/L in KCl, pH adjusted to 7 with KOH.
Solution B: 24 mmol/L in NaF, 100 mmol/L in KCl, pH at 6.2
Aspartic acid acts as a calcium fluoride inhibitor. The mean (n=3) F deposition was 1.73±0.32 $\mu$g/cm$^2$.

EXAMPLE V

Solution A: 20 mmol/L in calcium glycerophosphate and 100 mmol/L in KCl: pH 100 adjusted to 5.1 with HCl
Solution B: 24 mmol/L in NaF, 100 mmol/L in KCl, pH at 6.2
Glycerophosphoric acid acts as a calcium phosphate inhibitor and a weak calcium complexing agent. The mean (n=3) F deposition was 2.62±0.14 $\mu$g per cm$^2$ of enamel surface.

EXAMPLE VI

This example shows that an inhibitor added to the rinse at a lower F level produced the desired induction and good F deposition.

Solution A: 80 mmol/L in CaCl$_2$, 100 mmol/L in KCl, 0.5 mmol/L in Ca glycerophosphate, pH 7
Solution B: 12 mmol/L in NaF, 100 mmol/L in KCl, pH 7
The induction time was 23±2 seconds and F deposition was 2.45±0.76 $\mu$g/cm$^2$. This example also shows that the concept of using CaF$_2$, inhibitors in two-component F delivery systems is applicable in systems with different F concentrations. The F deposition from this rinse is almost the same as that from a rinse that contained twice as much F (2.62±0.16 µg/cm², Example V). However the data suggest that a greater variance is present in the rinse with the lower F concentration.

EXAMPLE VII

This example shows how the inventive two-component system can be used to formulate dentifrices. Dentifrices are chemically more complex than the rinses because they contain, among other things, abrasive particles, detergents, and nonaqueous liquids. However, the basic principle for precipitating calcium fluoride from a two-component system described above for the rinses can also be applied to dentifrices. The F content of dentifrice is higher (1000 ppm), but the recommended quantity per application is lower, e.g., 1 gram. Because of the high efficiency of the two-component system in depositing F, two-component dentifrices can produce larger F depositions even though the F contents were lower. A typical two-component dentifrice formulation studied consisted of:

Paste A: To 1000 grams of a non-fluoride dentifrice was added 40 mmols of calcium glycerophosphate; pH was adjusted to 5.1.

Paste B: To 1000 grams of a non-fluoride dentifrice was added 48 mmols of NaF; pH was adjusted to 5.1.

When equal amounts of pastes A and B are combined, the F content in the combined paste is 456 ppm, approximately half the amount of F found in commercially available fluoride dentifrices. In our experiments, 0.5 grams each of pastes A and B and 2 milliliters of water were blended to produce a homogenous slurry which was then applied to the tooth surface for one minute. The F deposition was measured using the same procedure as described above for the rinse studies. The F deposition produced by the test dentifrice was 1.28±0.56 (mean±S.D.; n=3) µg/cm². This value is about five times the F deposition produced by a commercially obtained dentifrice that contained 1000 ppm of F as NaF. Thus, the results indicate that with the inventive two-component system, a greater anti-caries effect can be produced from a dentifrice that has a lower F dose.

The preferred embodiment of the present invention is now fully described. The above description, however, is only illustrative of the invention and is not intended to limit the invention in spirit or scope. Only the following claims and their equivalents limit the scope of the invention.

We claim:

1. A two-component system for delayed sustained precipitation of calcium fluoride onto and into dental tissue, comprising:

(a) a first component containing a soluble calcium source, with no more than approximately ten percent of the calcium in complexed form, providing a calcium ion concentration of at least about 10 mmols per liter in the supersaturated solution ultimately formed by mixing the two components in an aqueous environment;

(b) a second component containing a soluble fluoride compound providing a fluoride concentration of at least about 3 mmols per liter in the supersaturated solution ultimately formed by mixing the two components in an aqueous environment, wherein the second component is isolated from reaction with the first component during storage and prior to use; and (c) at least one calcium fluoride inhibitor present in either or both of components and (a) and (b);

whereby when the two components are combined, the inhibitor produces a delay of at least about five seconds before significant formation of calcium fluoride occurs, and wherein the level of phosphate in the system is less than the concentration needed for significant precipitation of hydroxyapatite.

2. The system of claim 1 in the form of a dentrifice.

3. The system of claim 1 in the form of a mouth rinse.

4. The system of claim 1 in the form of a chewable tablet.

5. The system of claim 1 wherein the soluble calcium source is a salt of calcium which is non-toxic enough for oral use at the intended level on a regular basis and stable for the desired shelf life.

6. The system of claim 1 wherein the soluble calcium source is selected from the group consisting of calcium chloride, calcium acetate, calcium butylate, and calcium lactate.

7. The system of claim 6 wherein the calcium source is calcium chloride.

8. The system of claim 1 wherein the soluble fluoride compound is a compound which is non-toxic enough for use at the intended level on a regular basis and stable for the desired shelf life.

9. The system of claim 8 wherein the soluble fluoride compound is selected from the group consisting of sodium fluoride, stannous fluoride and potassium fluoride.

10. The system of claim 9 wherein the soluble fluoride compound is sodium fluoride or stannous fluoride.

11. The system of claim 1 wherein the second component is stored in a separate compartment from the first component prior to use.

12. The system of claim 1 wherein more than one calcium fluoride inhibitor is present.

13. The system of claim 1 wherein the calcium fluoride inhibitor is an inhibitor of both nucleation and crystal growth.

14. The system of claim 1 wherein the concentration of inhibitor in the supersaturated solution ultimately formed by mixing the two components in an aqueous environment is between 0.025 and 100 mmol per liter.

15. The system of claim 1 wherein the inhibitor is selected from the group consisting of orthophosphates, pyrophosphates, polyphosphates, glycerol phosphate, di-carboxylic acids, tri-carboxylic acids, tetra-carboxylic acids, phosphonates, and poly-carboxylic acids.

16. The system of claim 1 wherein the inhibitor is selected from the group consisting of orthophosphates, pyrophosphates, phytate, glycerophosphate, citric acid and EDTA.

17. The system of claim 1 wherein the inhibitor is phosphate and the concentration of phosphate in the solution ultimately formed by mixing the two components in an aqueous environment is less than 1 mmol per liter.

18. The system of claim 1 wherein two inhibitors are employed and the delay before significant formation of calcium chloride occurs is more than the sum of the delays induced when the inhibitors are used individually.

19. The system of claim 18 wherein the inhibitors are pyrophosphate and EDTA.

20. The system of claim 1 wherein the calcium fluoride precipitation continues throughout the intended period of application following the initial delay in formation of calcium fluoride.

21. The system of claim 20 wherein the intended period of application is between about 0.5 and 4 minutes.

22. The system of claim 20 wherein the intended period of application is about one minute.

23. The system of claim 1 wherein at least about 25 percent of the dissolved fluoride is precipitated out during the intended application period.

24. The system of claim 23 wherein the intended application time is about 1 minute.

25. The system of claim 1 wherein the calcium fluoride deposited in the dental tissue is present at a level of at least about 0.5 micrograms per centimeter squared.

26. A method for fluoridating dental tissue comprising mixing the two components of claim 1 and promptly applying the mixture to dental tissue.

* * * * *